(12) United States Patent
Schaeffer

(10) Patent No.: US 7,335,228 B2
(45) Date of Patent: Feb. 26, 2008

(54) STENT WITH RING ARCHITECTURE AND AXIALLY DISPLACED CONNECTOR SEGMENTS

(75) Inventor: Darin G. Schaeffer, Bloomington, IN (US)

(73) Assignee: Cook Incorporated, Bloomington, IN (US)

(*) Notice: Subject to any disclaimer, the term of this patent is extended or adjusted under 35 U.S.C. 154(b) by 638 days.

(21) Appl. No.: 10/814,610

(22) Filed: Mar. 30, 2004

(65) Prior Publication Data

US 2004/0243218 A1    Dec. 2, 2004

Related U.S. Application Data

(63) Continuation-in-part of application No. 10/267,576, filed on Oct. 8, 2002, now Pat. No. 6,786,922.

(51) Int. Cl.
*A61F 2/06* (2006.01)
(52) U.S. Cl. .................................................. 623/1.15
(58) Field of Classification Search ....... 623/1.15–1.17
See application file for complete search history.

(56) References Cited

U.S. PATENT DOCUMENTS

| 5,421,955 | A | 6/1995 | Lau et al. ...................... 216/48 |
| 5,449,373 | A | 9/1995 | Pinchasik et al. ........... 606/198 |
| 5,514,154 | A | 5/1996 | Lau et al. .................... 606/195 |
| 5,607,442 | A | 3/1997 | Fischell et al. ............. 606/191 |
| 5,697,971 | A | 12/1997 | Fischell et al. ................ 623/1 |
| 5,718,713 | A | 2/1998 | Frantzen ..................... 606/198 |
| 5,733,303 | A | 3/1998 | Israel et al. ................. 606/198 |
| 5,741,327 | A | 4/1998 | Frantzen ........................ 623/1 |
| 5,746,691 | A | 5/1998 | Frantzen ...................... 600/36 |
| 5,843,120 | A | 12/1998 | Israel et al. ................. 606/198 |
| 5,843,175 | A | 12/1998 | Frantzen ........................ 623/1 |
| 5,868,780 | A | 2/1999 | Lashinski et al. ........... 606/198 |
| 5,868,782 | A | 2/1999 | Frantzen ..................... 606/198 |
| 5,935,162 | A | 8/1999 | Dang ......................... 623/1.15 |
| 5,948,017 | A | 9/1999 | Taheri ....................... 623/1.14 |
| 5,972,018 | A | 10/1999 | Israel et al. ................. 606/198 |
| 6,019,789 | A | 2/2000 | Dinh et al. ..................... 623/1 |

(Continued)

FOREIGN PATENT DOCUMENTS

EP    0 958 794 A    11/1999

(Continued)

*Primary Examiner*—Corrine McDermott
*Assistant Examiner*—Cheryl Miller
(74) *Attorney, Agent, or Firm*—Brinks Hofer Gilson & Lione

(57) ABSTRACT

An expandable stent is provided. The stent has a ring architecture in which a plurality of connector segments join a plurality of ring structures to form the stent. The ring structures are an endless pattern of unit structures, each of which has two lateral arms and a central portion, and is inverted with respect to the immediately adjacent unit structures of the same ring structure. The connector segments have an undulating portion and can be axially displaced relative to other, circumferentially adjacent connector segments when the stent is in an unexpanded configuration. The stent can include axial portions in which connector segments are axially displaced from circumferentially adjacent connector segments, and can include other axial portions in which connector segments are axially aligned with circumferentially adjacent connector segments. A delivery system that includes a stent accordingly to the present invention is also provided.

20 Claims, 8 Drawing Sheets

U.S. PATENT DOCUMENTS

| | | | |
|---|---|---|---|
| 6,042,606 A | 3/2000 | Frantzen | 623/1 |
| 6,068,656 A | 5/2000 | Von Oepen | 623/1.17 |
| 6,071,298 A | 6/2000 | Lashinski et al. | 606/198 |
| 6,083,259 A | 7/2000 | Frantzen | 623/1.15 |
| 6,183,507 B1 | 2/2001 | Lashinski et al. | 623/1.15 |
| 6,193,744 B1 | 2/2001 | Ehr et al. | 623/1 |
| 6,217,608 B1 | 4/2001 | Penn et al. | 623/1.16 |
| 6,299,635 B1 | 10/2001 | Frantzen | 623/1.17 |
| 6,325,826 B1 * | 12/2001 | Vardi et al. | 623/1.35 |
| 6,352,552 B1 * | 3/2002 | Levinson et al. | 623/1.15 |
| 6,375,677 B1 | 4/2002 | Penn et al. | 623/1.16 |
| 6,416,543 B1 | 7/2002 | Hilaire et al. | 623/1.16 |
| 6,530,951 B1 | 3/2003 | Bates et al. | 623/1.45 |
| 6,602,281 B1 * | 8/2003 | Klein | 623/1.15 |
| 6,629,994 B2 * | 10/2003 | Gomez et al. | 623/1.15 |
| 6,652,573 B2 * | 11/2003 | von Oepen | 623/1.15 |
| 6,796,997 B1 * | 9/2004 | Penn et al. | 623/1.15 |
| 6,846,323 B2 * | 1/2005 | Yip et al. | 623/1.16 |
| 6,863,684 B2 * | 3/2005 | Kim et al. | 623/1.15 |
| 6,896,697 B1 * | 5/2005 | Yip et al. | 623/1.15 |
| 2002/0198593 A1 | 12/2002 | Gomez et al. | |
| 2006/0116751 A1 * | 6/2006 | Bayle et al. | 623/1.16 |

FOREIGN PATENT DOCUMENTS

| | | |
|---|---|---|
| WO | WO 99 11197 | 3/1999 |
| WO | WO 99 49811 A | 10/1999 |

* cited by examiner

STENT WITH RING ARCHITECTURE AND AXIALLY DISPLACED CONNECTOR SEGMENTS

CROSS REFERENCE TO PREVIOUS APPLICATION

This application is a continuation-in-part application of, and claims priority to, non-provisional application Ser. No. 10/267,576, filed on Oct. 8, 2002 now U.S. Pat. No. 6,786,922.

FIELD OF THE INVENTION

The present invention relates generally to the field of intraluminal support devices, or stents. More particularly, the present invention relates to balloon expandable and self-expanding stents having a ring structure architecture. Also, the invention relates to delivery and placement systems for deploying stents in a particular area within a body vessel.

BACKGROUND OF THE INVENTION

Various types of disease conditions present clinical situations in which a vessel of a patient needs to be artificially supported to maintain an open passageway through which fluids, such as blood, can flow. For example, blood flow through an artery can be impeded due to a build-up of cholesterol on the interior wall of the vessel. Also, vessel walls can be weakened be a variety of conditions, such as aneurysms.

Intraluminal support frames, sometimes referred to as stents, provide an artificial mechanism to support a body vessel. Stents are typically tubular-shaped members that are placed in the lumen of the vessel and, once deployed, exert a radially-outward directed force onto the vessel wall to provide the desired support.

Stents are typically positioned at the point of treatment by navigation through the vessel, and possibly other connected vessels, until the point of treatment is reached. This navigation requires the stent to be able to move axially through the vessel(s) prior to deployment, while still maintaining the ability to exert an outward force on the interior wall once deployed. Accordingly, stents typically have radially unexpanded and expanded configurations. In the unexpanded configuration, the stent has a relatively small diameter that allows it to move axially through the vessel. In the expanded configuration, the stent has a relatively large diameter that allows it to exert an outward force on the interior wall of the lumen, thereby providing the desired support to the vessel.

During navigation through the vessel(s), the stent will likely encounter various turns and bends, which requires the stent to have a degree of longitudinal flexibility. Various stent configurations exist in the art that provide this desired flexibility to some degree. One approach utilizes a plurality of interconnected rings. The members that connect the rings provide the stent with flexibility. Unfortunately, the longitudinal flexibility can result in localized radial movement in the stent when the stent encounters a turn or bend. For example, one portion of a ring member may separate from an underlying balloon, which can interfere with navigation.

SUMMARY

The present invention provides a stent that includes a ring architecture and axially displaced connector segments. The stent has longitudinal flexibility that facilitates navigation of vessel turns and bends while maintaining stent portions close to the underlying components of the delivery device, such as a balloon and/or catheter. Preferably, the connector segments lie in a circumferentially extending zig-zag pattern.

In one embodiment, a stent according to the present invention comprises a plurality of ring structures, each of which comprises an endless pattern of unit structures. Each unit structure has two lateral arms and a central region disposed therebetween. The central region preferably comprises a peak disposed between two valleys. Also, each unit structure preferably is inverted with respect to the circumferentially adjacent unit structures of the same ring structure. A plurality of connector segments join each pair of ring structures in the stent. Preferably, each connector segment has an undulating portion. Particularly preferable, the undulating portions of circumferentially adjacent connector segments are axially displaced relative to each other. More preferred, the undulating portions of circumferentially adjacent connector segments are axially displaced when the stent is in a radially unexpanded configuration, and axially aligned when the stent is in a radially expanded configuration.

In another embodiment, a stent according to the invention comprises first and second ring structures individually comprising an endless undulating pattern and disposed axially adjacent each other, and a first plurality of connector segments joining the first and second ring structures. A third ring structure also comprises an endless undulating pattern and is disposed axially adjacent the first ring structure. A second plurality of connector segments joins the first and third ring structures. Each connector segment of the first and second plurality of connector segments has an undulating portion. The undulating portion of each connector segment of the first plurality of connector segments is axially displaced from the undulating portion of a circumferentially adjacent connector segment when the stent is in its unexpanded configuration. The undulating portion of each connector segment of the second plurality of connector segments is axially aligned with the undulating portion of a circumferentially adjacent connector segment when the stent is in the unexpanded configuration.

In another embodiment, a stent according to the invention comprises first and second axial portions. The first axial portion comprises a first plurality of ring structures joined by axially displaced connector segments and the second axial portion comprises a second plurality of ring structures joined by axially aligned connector segments.

In another embodiment, a stent according to the invention comprises a plurality of ring structures joined by a plurality of connector segments. Each of the plurality of connector segments has an undulating portion. A first set of the plurality of connector segments are axially aligned with and a second set of the plurality of connector segments are axially displaced from respective circumferentially adjacent connector segments.

The invention also provides a delivery system for placing a stent at a point of treatment in a vessel. In one embodiment, the delivery system comprises a catheter having a balloon positioned on a distal end. A connector assembly is positioned at a proximal end of the catheter and is adapted to facilitate expansion of the balloon. A stent according to the present invention is disposed on the distal end of the catheter, surrounding the balloon. Prior to placement, the stent is in an unexpanded configuration in which circumferentially adjacent connector segments joining adjacent ring structures are axially displaced relative to each other.

While the invention is defined by the claims appended hereto, additional understanding of the invention can be gained by reference to the attached drawings and the description of preferred embodiments presented below.

DETAILED DESCRIPTION OF VARIOUS EMBODIMENTS OF THE INVENTION

The following description of preferred embodiments of the invention provides examples of the present invention. The embodiments discussed herein are merely exemplary in nature, and are not intended to limit the scope of the invention in any manner. Rather, the description of these preferred embodiments serves to enable a person of ordinary skill in the relevant art to make and use the present invention.

Figure 1:
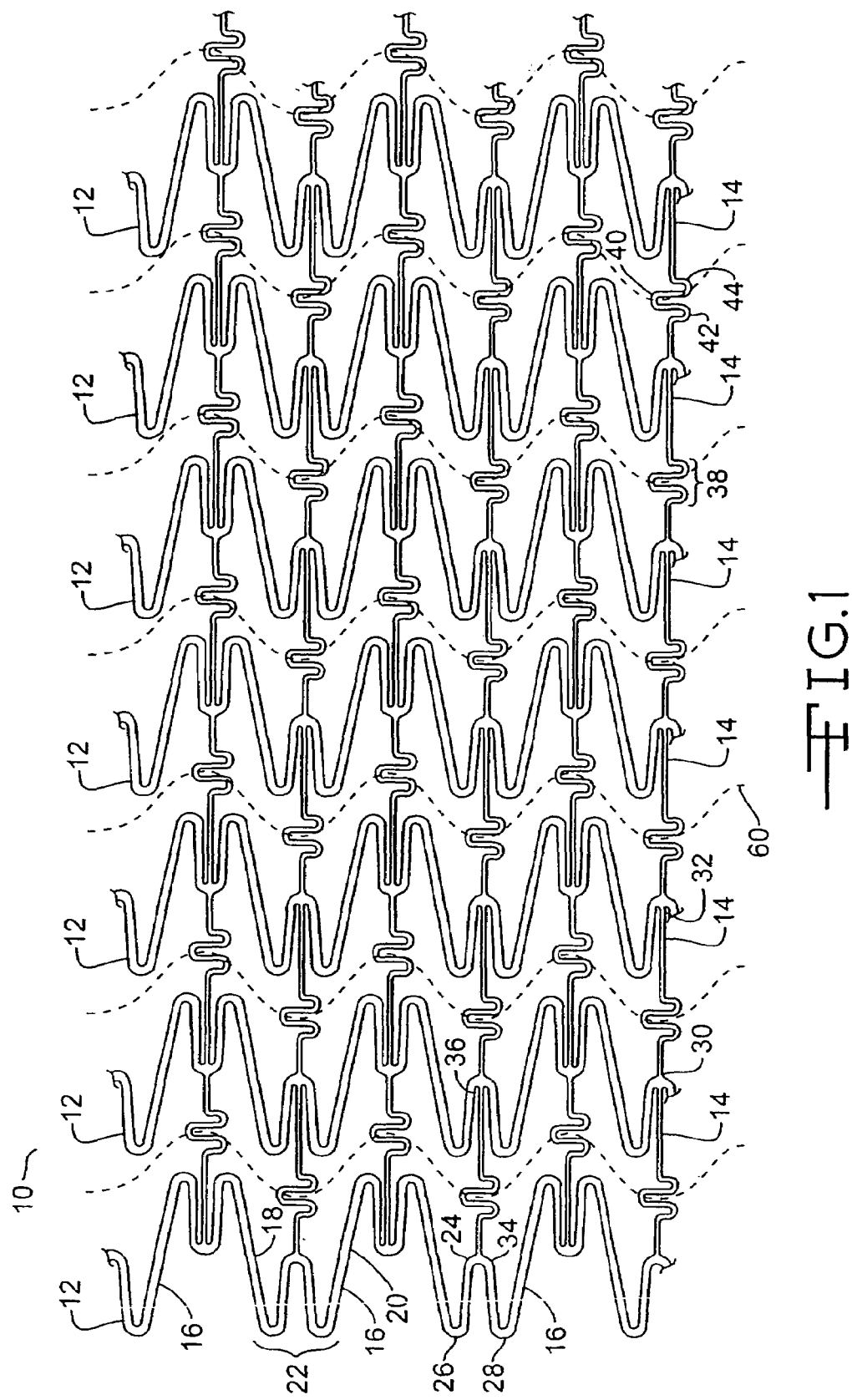
FIG. 1 is a flat pattern view of a stent according to a first preferred embodiment of the invention shown in an unexpanded configuration.

FIG. 1 illustrates a stent 10 according to a first preferred embodiment of the invention. The stent 10 comprises a plurality of ring structures 12 interconnected by a plurality of connector segments 14.

Each ring structure 12 is a substantially circular ring comprising an endless undulating pattern. Preferably, the undulating pattern comprises a serpentine pattern. Particularly preferable, the pattern comprises a plurality of unit structures 16. The unit structure 16 represents a specific configuration of the wire member that comprises a basic structural component of the stent 10. As used herein, the term wire refers to any filamentary member, including, but not limited to, drawn wire and filaments laser cut from a cannula.

Preferably, as illustrated in FIG. 1, the unit structure 16 comprises first 18 and second 20 lateral arms and a central region 22 disposed between the lateral arms 18, 20. The central region 22 defines a plurality of peaks and valleys in the structural member. Preferably, the central region 22 has a peak 24 disposed between first 26 and second 28 valleys. It should be noted that, as used herein, the terms peak and valley are interchangeable and both refer to a turn or bend in the ring structure 12. When used relative to each other, a peak refers to a turn in the opposite orientation of an adjacent valley, and vice versa.

This preferred configuration for the unit structure 16 generally provides a "W"-shaped structure for the unit structure 16. This "W" configuration provides many advantages. First, the "W" configuration is easily repeated around the circumference of the ring structures 12. As illustrated in FIG. 1, the unit structures 16 are preferably repeated one after another around the circumference of each ring structure 12. The "W" configuration facilitates this repeating when circumferentially adjacent unit structures 16 are inverted with respect to each other. Thus, as illustrated in FIG. 1, each ring structure 12 preferably comprises a series of unit structures 16, each of which has a "W" configuration and is inverted with respect to the immediately adjacent unit structure 16. In this preferred arrangement, circumferentially adjacent unit structures 16 share a common lateral arm 18, 20. Another advantage provided by the "W" configuration is the availability of central attachment points for connecting members, as will be described more fully below.

The ring structures 12 are interconnected to form the stent 10 by a plurality of connector segments 14. As illustrated in FIG. 1, each connector segment 14 joins first and second ring structures 12 and is preferably disposed between two axially adjacent unit structures 16 on these ring structures 12. Preferably, each connector segment 14 is disposed between peaks 24 of the two unit structures 16.

Each connector segment 14 has a first end 30 and a second end 32. In the unit structure 16, each peak 24 has a first side 34 and a second side 36. Each of the plurality of connector segments 14 is preferably positioned in a manner such that each of the first ends 30 is connected to a first side 34 of a peak 24 in a unit structure 16, and each second end 32 is connected to a second side 36 of a peak 24 in a unit structure 16 of an axially adjacent ring structure 12.

Figure 2:
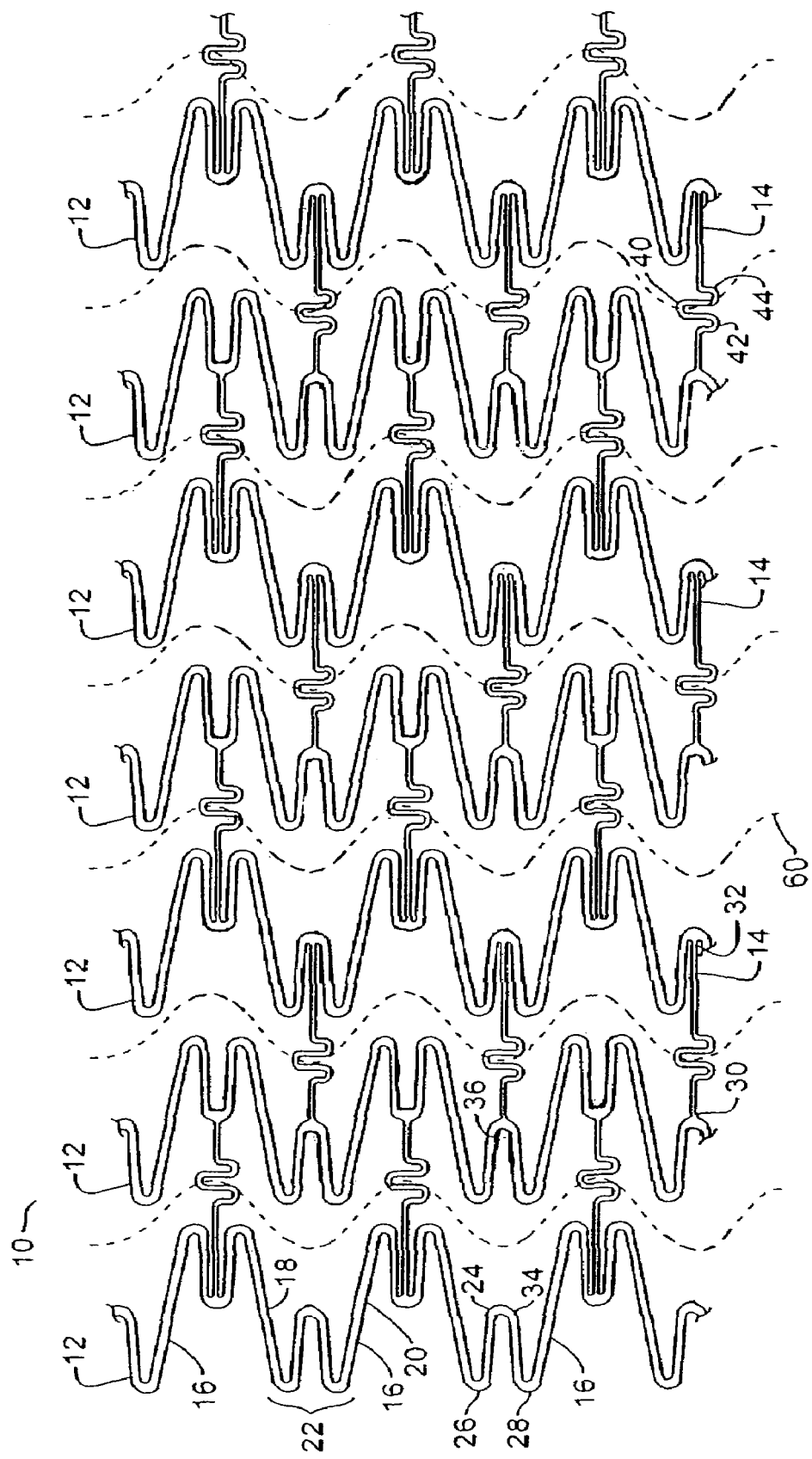
FIG. 2 is a flat pattern view of a stent according to an alternative embodiment of the present invention shown in an unexpanded configuration.

Also preferable, as illustrated in FIG. 1, each unit structure 16 of each ring structure 12 is connected to at least one connector segment 14. Particularly preferable, also as illustrated in FIG. 1, each unit structure 16 of each ring structure 12 is connected to two connector segments 14, excepting only unit structures 16 of the terminal ring structures 12. Alternatively, fewer connector segments 14 can be utilized. For example, FIG. 2 illustrates an alternative embodiment in which, for each adjacent pair of ring structures 12, a connector segment 14 is disposed between every other pair of adjacent unit structures 16. This use of fewer connector segments imparts additional flexibility onto the stent 10.

Each connector segment 14 also includes an undulating portion 38 that comprises one or more bends. The undulating portion 38 provides longitudinal flexibility to the stent 10 by providing a region with structural features that allow for localized lengthening. A variety of numbers and configurations of bends can be used in the undulating portion 38. Examples of suitable configurations include those having multiple bends that form a section that provides the desired longitudinal flexibility by allowing localized longitudinal extension of the undulating portion 38.

The connector segments 14 shown in FIG. 1 illustrate a preferred configuration for the undulating portions 38. In this preferred embodiment, each undulating portion 38 comprises a first u-shaped bend 40 disposed between second 42 and third 44 u-shaped bends. Preferably, the first u-shaped bend 40 extends in a first direction, and the second 42 and third 44 u-shaped bends extend in a second direction. Particularly preferable, the second direction is substantially opposite the first direction.

Figure 3:
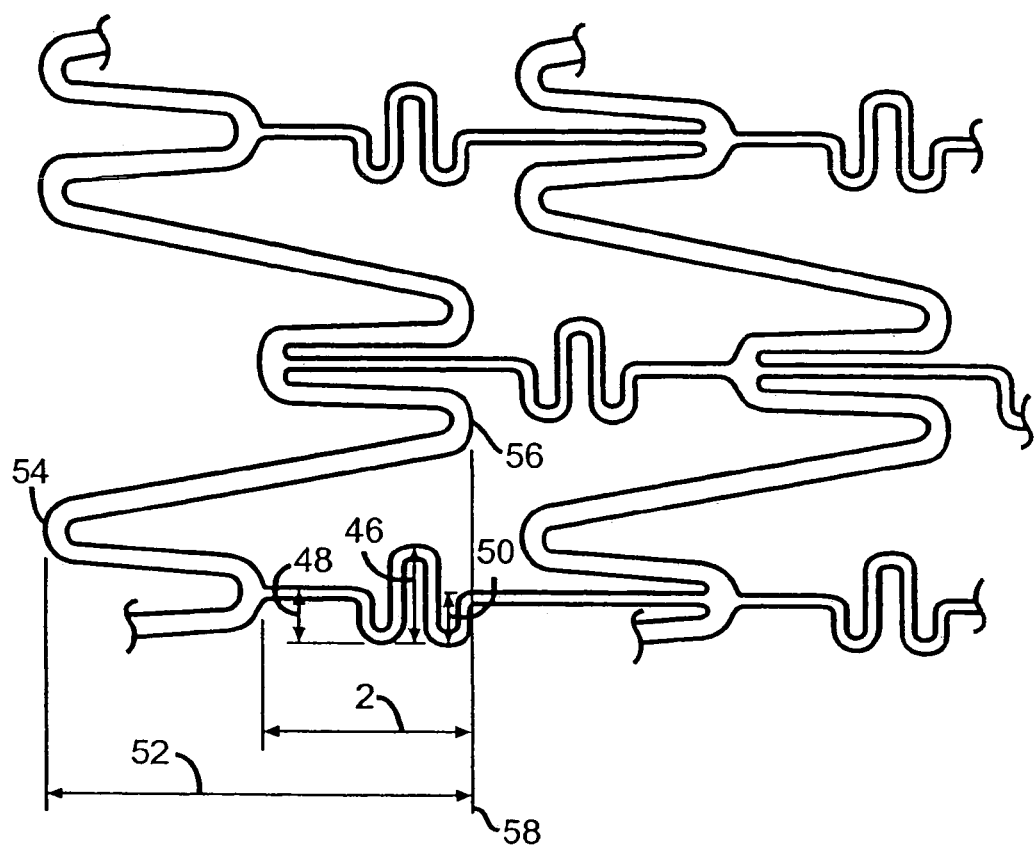
FIG. 3 is a magnified view of the flat pattern illustrated in FIG. 1.

Preferably, as best illustrated in FIG. 3, the first u-shaped bend 40 has a height 46 that is greater than a depth 48 of the second u-shaped bend 42. Also preferable, the depth 48 of the second u-shaped bend 42 is substantially the same as the depth 50 of the third u-shaped bend 44. This configuration simplifies manufacture due to its repeating nature and provides longitudinal flexibility for the stent 10.

Also, as best illustrated in FIG. 3, the undulating portion 38 preferably is axially positioned within the length 52 of a lateral arm 18, 20 of the unit structure 16 to which the connector segment 14 is attached. That is, each lateral arm 18, 20 has first 54 and second 56 ends, and the undulating portion 38 is preferably axially positioned between these ends 54, 56. Particularly preferable, as illustrated in FIG. 3, an edge 58 of the undulating portion 38 extends to substantially the same axial position as at least one of the first 26 and second 28 valleys of the unit structure 16. This configuration provides the desired longitudinal flexibility while maintaining radial strength of the stent 10.

As best illustrated in FIG. 1, adjacent ring structures 12 are preferably aligned in phase with each other. That is, adjacent ring structures 12 are preferably aligned such that axially adjacent unit structures 16 lie in complementary positions to each other. Particularly preferable, all ring structures 12 of the stent 10 are aligned in this manner.

A first series of circumferentially adjacent connector segments 14 join in axially adjacent ring structures 12. Preferably, circumferentially adjacent connector segments 14 are axially displaced relative to each other. This preferred arrangement arises in the preferred embodiment due to the inverted relationship between adjacent unit structures 16 within a single ring structure 12 and the alternating of the connection point between the connector segment 14 and the peak 24 from the first side 34 in one unit structure 16 to the second side 36 in the axially adjacent unit structure 16. This displacement maintains the desired longitudinal flexibility while also contributing to the radial strength of the stent 10.

In the preferred embodiment, as best illustrated in FIG. 1, the axial displacement of circumferentially adjacent connector segments 14 forms a zig-zag pattern 60 between undulating portions 38 of the series of connector segments 14 joining first and second ring structures 12. The zig-zag pattern 60 provides the benefits of the axial displacement, as indicated above, while providing a pattern that is readily manufactured due to its regular, repeating nature.

The stent 10 is an expandable stent having radially unexpanded and expanded configurations. As such, the stent 10 can be either a self-expanding stent, such as one fabricated from a shape memory material such as Nitinol, or a balloon expandable stent. FIG. 1 illustrates the stent 10 in its radially unexpanded configuration. In this configuration, which is conventionally used to minimize the radial dimension of the stent in order to facilitate placement into and navigation through a body vessel, circumferentially adjacent connector segments 14 are preferably arranged in the axially displaced manner described above. Particularly preferable, also as described above, the connector segments 14 are preferably arranged such that the undulating portions 38 are axially displaced relative to each other.

Figure 4:
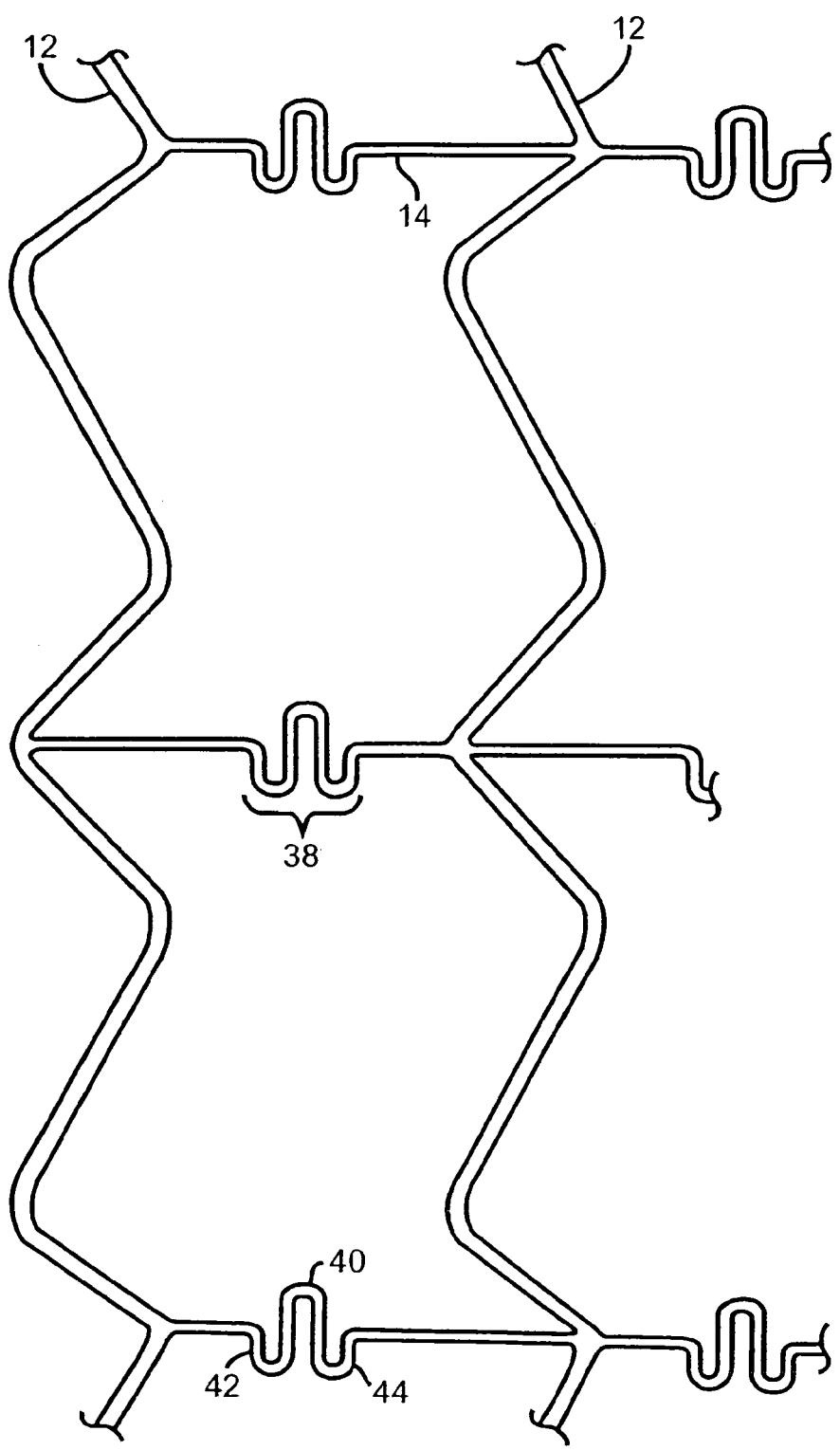
FIG. 4 is a magnified flat pattern view of the stent illustrated in FIG. 1 shown in an expanded configuration.

Once expanded, the connector segments 14 preferably deviate from the axial displacement of the unexpanded configuration. FIG. 4 illustrates the stent 10 of FIG. 1 in its expanded configuration. Preferably, upon expansion, the connector segments 14 substantially align axially such that they are no longer, or minimally, displaced relative to circumferentially adjacent connector segments 14. Particularly preferable, the undulating portions 38 of all connector segments 14 joining adjacent ring structures 12 are substantially axially aligned when the stent 10 is in this expanded configuration.

Figure 5:
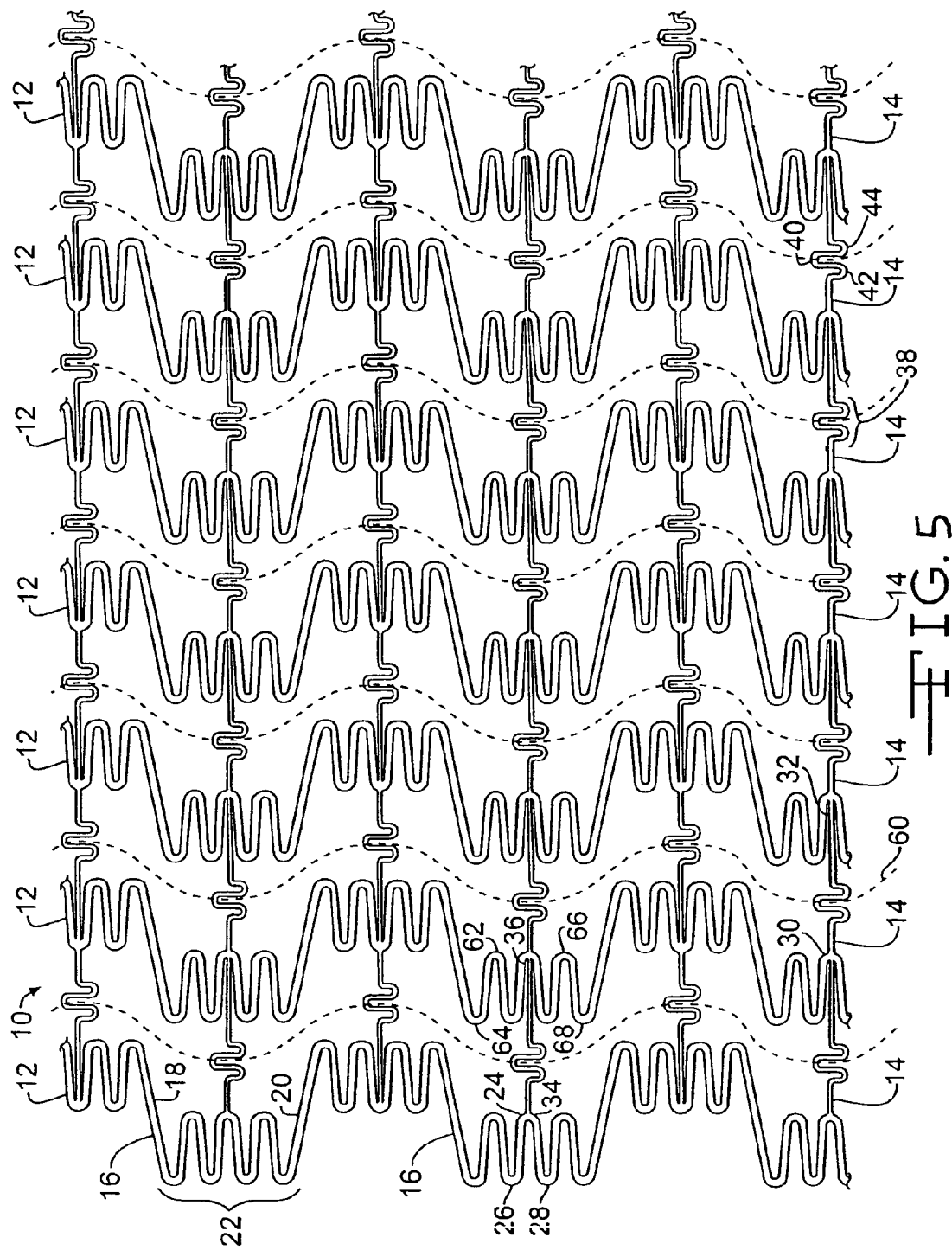
FIG. 5 is flat pattern view of a stent according to a second preferred embodiment of the invention shown in an unexpanded configuration.

FIG. 5 illustrates a stent according to another preferred embodiment of the present invention. In this embodiment the stent 10 includes a modified unit structure 16. The remainder of the stent 10, including the ring structure 12 and the connector segments 14, are preferably the same as described above for the first preferred embodiment.

Figure 6:
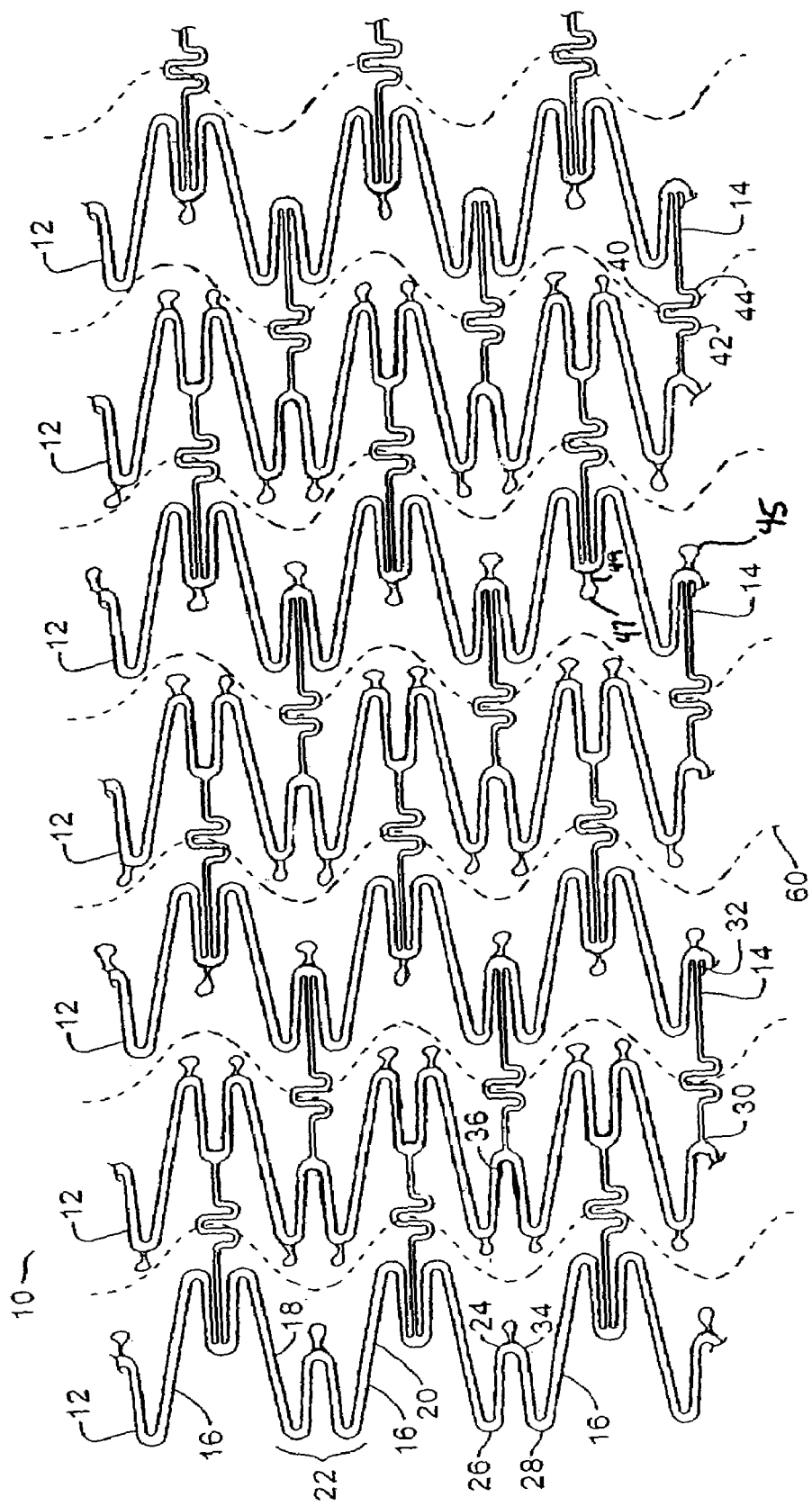
FIG. 6 is a flat pattern view of a stent according to a third preferred embodiment of the invention shown in an unexpanded configuration.

In this embodiment, the unit structure 16 is modified to include additional peaks and valleys. This modified design allows the stent 10 to have a relatively larger circumference, thereby making the stent useful in larger vessels. The modified unit structure 16 can include any suitable number of additional peaks and/or valleys as required for the larger vessel in which the stent 10 is to be utilized. FIG. 5 illustrates a preferred configuration in which the unit structure 16 includes a second peak 62, a third valley 64, a third peak 66, and a fourth valley 68. As illustrated in the figure, the connector segment 14 preferably is connected to the first peak 24, as in the first preferred embodiment. However, the connector segment 14 can also be connected to one of the additional peaks 56, 66 and/or valleys 64, 68.

in another preferred embodiment, illustrated in FIG. 6, the stent 10 further includes one or more pads 45. The pads 45 are outwardly projecting surfaces that extend from the structural member of the ring structures 12. The pads 45 are preferably defined by the structural member of the ring structure, and preferably have an enlarged region 47 spaced from the structural member by a narrower throat region 49. As illustrated in the Figure the pads 45 are preferably positioned on the peaks 24 and valleys 26, 28 not connected to a connecting member 14.

The pads 45 provide a surface suitable for deposition of material. For example, a therapeutic, such as a pharmaceutical composition, can be disposed on the pad 45. This placement on the pad allows the stent 10 to deliver the material, e.g., the therapeutic, to a treatment site within a body vessel Any suitable material can be utilized in conjunction with the pads, and examples of suitable materials include pharmaceutical compositions. The pharmaceutical composition utilized will depend on the desired therapy. Examples of suitable pharmaceutical composition include, but are not limited to, heparin, covalent heparin or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric-oxide promoter or another vasodilator; an antimicrobial agent or antibiotic; aspirin, ticlopidine, a glycoprotein IIb/IIIa inhibitor or another inhibitor of surface glycoprotein receptors, or another antiplatelet agent; colchicine or another antimitotic, or another microtubule inhibitor, dimethylsulfoxide (DMSO), a retinoid or another antisecretory agent; cytochalasin or another actin inhibitor; or a remodeling inhibitor; deoxyribonucleic acid, an antisense nucleotide or another agent for molecular genetic intervention; methotrexate or another antimetabolite or antiproliferative agent; paclitaxel; tamoxifen citrate, Taxol® or derivatives thereof, or other anti-cancer chemotherapeutic agents; dexamethasone, dexamethasone sodium phosphate, dexamethasone acetate or another dexamethasone derivative, or another anti-inflammatory steroid or non-steroidal anti-inflammatory agent; cyclosporin, sirolimus, or another immunosuppressive agent; tripodal (aPDGF antagonist), angiopeptin (a growth hormone antagonist), angiogenin or other growth factors, or an anti-growth factor antibody, or another growth factor antagonist; dopamine, bromocriptine mesylate, pergolide mesylate or another dopamine agonist; $^{60}$Co, $^{192}$Ir, $^{32}$P, $^{111}$In, $^{90}$Y, $^{99m}$Tc or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-amino steroid (lasaroid) or another free radical scavenger, iron chelator or antioxidant; a $^{14}$C-, $^{3}$H-, $^{131}$I-, $^{32}$P- or $^{36}$S-radiolabelled form or other radiolabelled form of any of the foregoing; estrogen or another sex hormone; AZT or other antipolymerases; acyclovir, famciclovir, rimantadine hydrochloride, ganciclovir sodium or other antiviral agents; 5-aminolevulinic acid, meta-tetrahydroxyphenylchlorin, hexadecaflouoro zinc phthalocyanine, tetramethyl hematoporphyrin, rhodamine 123 or other photodynamic therapy agents; an IgG2 Kappa antibody against Pseudomonas aeruginosa exotoxin A and reactive with A431 epidermoid carcinoma cells, monoclonal antibody against the noradrenergic enzyme dopamine betahydroxylase conjugated to saporin or other antibody target therapy agents; enalapril or other prodrugs; and gene therapy agents, or a mixture of any of these.

Stents according to the present invention can be fabricated by any suitable process known in the art. The fabrication process need only be able to produce the ring architecture and connector segments of the invention. For self-expanding stents, in a preferred method, a thread of suitable material can be weaved an/or configured into appropriate form. For balloon-expanded stents, in a preferred method, the stent is preferably fabricated from an initially solid tube of appropriate material by etching or cutting away unused portions to leave a stent with the desired pattern.

The stent can also be fabricated from any suitable material. The material need only be medically acceptable, i.e., biocompatible, and provide the desired longitudinal flexibility and radial strength. Examples of suitable materials include shape memory alloys, such as Nitinol, and stainless steel.

Figure 7:
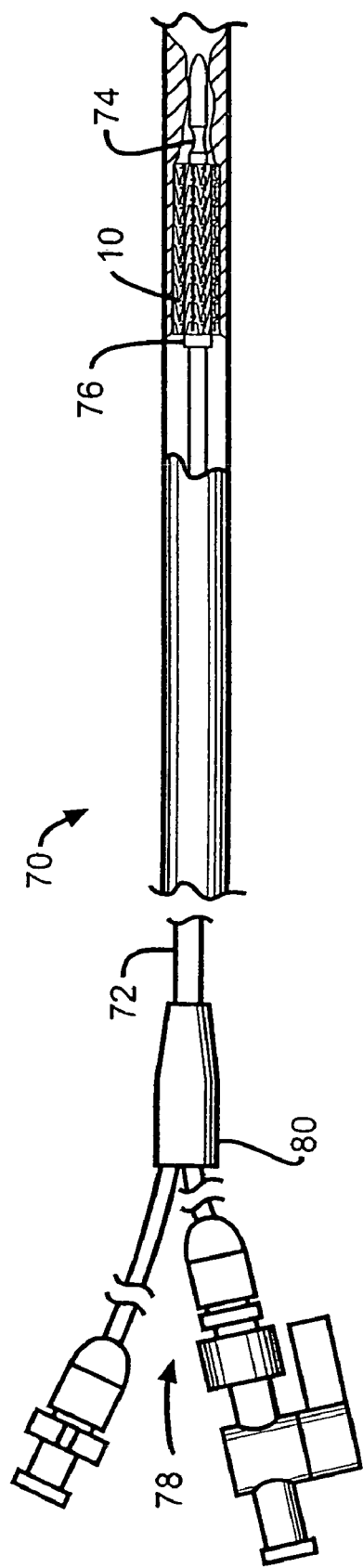
FIG. 7 is a partial sectional view of a delivery system partially placed within a body vessel according to a preferred embodiment of the invention.

FIG. 7 illustrates a delivery system 70 according to a preferred embodiment of the present invention. In this embodiment, the delivery system 70 includes a catheter 72 having a distal end 74. A balloon 76 is positioned on the distal end 74 of the catheter 72 in the conventional manner. A connector assembly 78 is disposed at the proximal end 80 of the catheter 72 and is adapted to facilitate expansion of the balloon 76 as is known in the art. The connector assembly 78 provides access to an interior lumen of the catheter 72 to provide access to the balloon 76, and possibly a guidewire (not illustrated) or other conventional component.

A balloon expandable stent 10 according to the present invention is disposed on the distal end 74 of the catheter 72. The stent 10 surrounds the balloon 76 and is initially, prior to placement in a body vessel, in its unexpanded configuration. This positioning allows the balloon 76, upon inflation, to expand the stent 10 into its expanded configuration.

As indicated above, the present invention is well-suited for providing artificial support to a body vessel in need of such support. This can be performed by inserting the distal end 74 of the catheter 72 into a body vessel and navigating the distal end 74, and the surrounding stent 10, to a point in a vessel in need of artificial support. The catheter 72 can be placed over a guidewire (not illustrated) to facilitate navigation. Once the stent 10 is at the point of treatment, the balloon 76 can be inflated in the conventional manner. Inflation of the balloon 76 forces the stent 10 to expand. During expansion, in which the stent 10 changes from its unexpanded configuration to its expanded configuration, circumferentially adjacent connector segments 14 deviate from the axially-displaced configuration associated with the unexpanded configuration of the stent 10, becoming substantially aligned in the axial direction. Following expansion, the balloon 76 is deflated, leaving the stent 10 in its expanded configuration. The catheter 72 is then withdrawn from the vessel, leaving the stent in its expanded configuration at the point of treatment.

The stents of the invention can be delivered by various types of delivery devices and techniques, including over-the-wire and rapid-exchange delivery systems and techniques.

Figure 8:
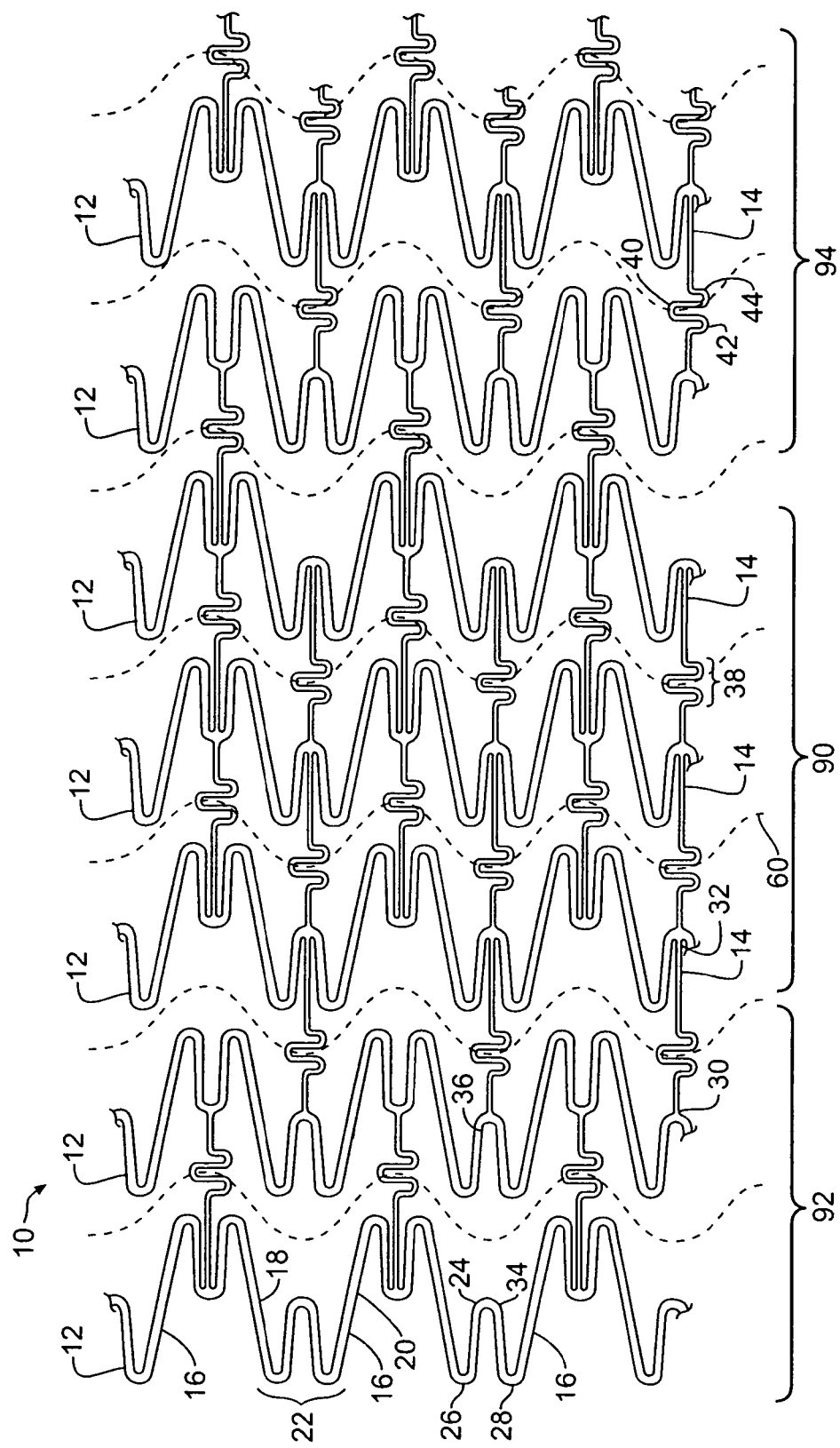
FIG. 8 is a flat pattern view of a stent according to another embodiment of the invention shown in an unexpanded configuration.

FIG. 8 illustrates a stent 10 according to another embodiment of the invention. In this embodiment, the stent 10 comprises a plurality of ring structures 12 interconnected by a plurality of connector segments 14. Both the ring structures 12 and connector segments 14 are identical to those described above for other embodiments of the invention. Accordingly, the reference numbers in FIG. 8 refer to the same features and/or components described above.

As in the other embodiments, the connector segments 14 join adjacent pairs of ring structures 12. In this embodiment, the stent 10 has multiple axial portions 90, 92, 94. The axial portions 90, 92, 94 comprise portions of the stent 10 in which the connector segments 14 are either displaced from or aligned with circumferentially adjacent connector segments 14. For example, axial portion 90 includes a plurality of connector segments 14, each of which is axially displaced from a circumferentially adjacent connector segment 14. In contrast, axial portions 92 and 94 include a plurality of connector segments 14, each of which is axially aligned with a circumferentially adjacent connector segment 14.

Stents according to the invention can include two or more of these different types of axial portions. For example, as illustrated in FIG. 8, a stent 10 according to the invention can include two portions 92, 94 in which the connector segments 14 are axially aligned, and one portion 90 in which the connector segments 14 are axially displaced. The precise number of each type of axial portion chosen will depend on numerous factors, including the desired overall flexibility of the stent 10. By including a greater number of axial portions, such as portions 92, 94, in which the connector segments 14 are axially aligned, a stent according to the invention can have a greater overall flexibility. By including a greater number of axial portions, such as portion 90, in which the connector segments 14 are axially displaced, a stent according to the invention can have an area with greater radial strength.

Additionally, stents according to the invention can include any suitable arrangement of the various types of axial portions. For example, as illustrated in FIG. 8, two portions 92, 94 in which connector segments 14 are axially aligned can be disposed at respective ends of the stent 10. A portion 90 in which the connector segments 14 are axially displaced can be disposed between the end portions 92, 94. In this arrangement, the portion 90 can provide additional radial strength to the stent 10 at a point where such additional strength is desired, such as a point at which the stent 10 may contact a stenosis. Also, the arrangement of portions 92, 94 at ends of the stent can provide increased flexibility to the stent at these locations. This may enhance the ability of the stent to navigate through tortuous paths of the vasculature. The exact arrangement of axial portions chosen would depend on several factors, including the need for flexibility at certain axial portions of the stent, and the need for increased radial strength at other axial portions of the stent.

The foregoing disclosure includes the best mode devised by the inventor for practicing the invention. It is apparent, however, that several variations in intraluminal graft assemblies in accordance with the present invention may be conceivable by one skilled in the art. Inasmuch as the foregoing disclosure is intended to enable one skilled in the pertinent art to practice the instant invention, it should not be construed to be limited thereby, but should be construed to include such aforementioned variations. As such, the present invention should be limited only by the spirit and scope of the following claims.

What is claimed is:

1. A stent having expanded and unexpanded configurations, said stent comprising:
    first and second ring structures individually comprising an endless undulating pattern and disposed axially adjacent each other;
    a first plurality of connector segments joining the first and second ring structures, each of the first plurality of connector segments having an undulating portion;
    a third ring structure comprising an endless undulating pattern and disposed axially adjacent the second ring structure; and
    a second plurality of connector segments joining the second and third ring structures, each of the second plurality of connector segments having an undulating portion;
    a fourth ring structure comprising an endless undulating pattern and disposed axially adjacent the third ring structure; and
    a third plurality of connector segments joining the third and fourth ring structures, each of the third plurality of connector segments having an undulating portion;
    a fifth ring structure comprising an endless undulating pattern and disposed axially adjacent the fourth ring structure; and
    a fourth plurality of connector segments joining the fourth and fifth ring structures, each of the fourth plurality of connector segments having an undulating portion;
    a sixth ring structure comprising an endless undulating pattern and disposed axially adjacent the fifth ring structure; and
    a fifth plurality of connector segments joining the fifth and sixth ring structures, each of the fifth plurality of connector segments having an undulating portion;
    a seventh ring structure comprising an endless undulating pattern and disposed axially adjacent the sixth ring structure; and
    a sixth plurality of connector segments joining the sixth and seventh ring structures, each of the sixth plurality of connector segments having an undulating portion;
    wherein said endless undulating pattern comprises a serpentine pattern, said serpentine pattern comprising a plurality of unit structures, each unit structure comprising first and second lateral arms and a central region disposed between said first and second lateral arms, said central region having at least a peak disposed between first and second valleys, wherein the peak is shorter than the first and second lateral arms, each said unit structure being inverted with respect to circumferentially adjacent unit structures, wherein the lateral arms of each unit structure are shared with adjacent unit structures;
    wherein the undulating portion of each connector segment of the third and fourth plurality of connector segments is axially displaced from the undulating portion of a circumferentially adjacent connector segment when the stent is in said unexpanded configuration; and
    wherein the undulating portion of each connector segment of the first, second, fifth and sixth plurality of connector segments is axially aligned with the undulating portion of a circumferentially adjacent connector segment when the stent is in said unexpanded configuration.

2. The stent of claim 1, further comprising one or more pads extending outward from at least one of said first, second, third, fourth, fifth, sixth or seventh ring structures.

3. The stent of claim 2, wherein each of said one or more pads comprises an enlarged region spaced from at least one of said first, second, third, fourth, fifth, sixth or seventh ring structures by a narrow throat region.

4. The stent of claim 2, further comprising a pharmaceutical composition disposed on said one or more pads.

5. The stent of claim 4, wherein said pharmaceutical composition is selected from the group consisting of heparin, covalent heparin or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; aspirin, ticlopidine, a glycoprotein lib/IIla inhibitor or another inhibitor of surface glycoprotein receptors, or another antiplatelet agent; colchicine or another antimitotic, or another microtubule inhibitor, dimethylsulfoxide (DMSO), a retinoid or another antisecretory agent; cytochalasin or another actin inhibitor; or a remodeling inhibitor; deoxyribonucleic acid, an antisense nucleotide or another agent for molecular genetic intervention; methotrexate or another antimetabolite or antiproliferative agent; paclitaxel; tamoxifen citrate, Taxol® or derivatives thereof, or other anti-cancer chemotherapeutic agents; dexamethasone, dexamethasone sodium phosphate, dexamethasone acetate or another dexamethasone derivative, or another anti-flammatory steroid or non-steroidal anti-inflammatory agent; cyclosporin, sirolimus, or another immunosuppressive agent; tripodal (aPDGF antagonist), angiopeptin (a growth hormone antagonist), angiogenin or other growth factors, or an anti-growth factor antibody, or another growth factor antagonist; dopamine, bromocriptine mesylate, pergolide mesylate or another dopamine agonist; $^{60}$Co, $^{192}$Ir, $^{32}$P, $^{111}$In, $^{90}$Y, $^{99m}$Tc or another radiotherapeutic agent; iodine-containing compounds, barium-containing compounds, gold, tantalum, platinum, tungsten or another heavy metal functioning as a radiopaque agent; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-amino steroid (lasaroid) or another free radical scavenger, iron chelator or antioxidant; $^{14}$C-, $^{3}$H-, $^{131}$I-, $^{32}$P- or $^{36}$S-radiolabelled form or other radiolabelled form of any of the foregoing; estrogen or another sex hormone; AZT or other antipolymerases; acyclovir, famciclovir, rimantadine hydrochloride, ganciclovir sodium or other antiviral agents; 5-aminolevulinic acid, meta-tetrahydroxyphenylchlorin, hexadecaflouoro zinc phthalocyanine, tetramethyl hematoporphyrin, rhodamine 123 or other photodynamic therapy agents; an IgG2Kappa antibody against Pseudomonas aeruginosa exotoxin A and reactive with A431epidermoid carcinoma cells, monoclonal antibody against the noradrenergic enzyme dopamine betahydroxylase conjugated to saporin or other antibody target therapy agents; enalapril or other prodrugs; and gene therapy agents.

6. The stent of claim 1, wherein each of the first, second, third, fourth, fifth and sixth plurality of connector segments is joined at one end to one of the peaks of the central regions and is joined at another end to another of the peaks of the central regions.

7. The stent of claim 6, wherein each of the first, second, third, fourth, fifth and sixth plurality of connector segments is generally straight along a longitudinal axis of the stent.

8. The stent of claim 7, wherein the undulating portion comprises a first u-shaped bend disposed between second and third u-shaped bends.

9. The stent of claim 8, wherein the first u-shaped bend extends in a first direction and the second and third u-shaped bends extend in a second direction.

10. The stent of claim 9, wherein the second direction is substantially opposite the first direction.

11. A stent having expanded and unexpanded configurations, said stent comprising:
   a series of ring structures forming serpentine patterns comprising a plurality of unit structures, each unit structure comprising first and second lateral arms and a central region disposed between said first and second lateral arms, said central region having at least a peak disposed between first and second valleys, wherein the peak is shorter than the first and second lateral arms, each of said unit structures being inverted with respect to circumferentially adjacent unit structures, wherein the lateral arms of each unit structure are shared with the adjacent unit structures;
   a first axial portion of the stent comprises at least two of the ring structures being joined by a first plurality of connector segments, each of the first plurality of connector segments having an undulating portion;
   a second axial portion of the stent comprises at least two of the ring structures being joined by a second plurality of connector segments, each of the second plurality of connector segments having an undulating portion;
   a third axial portion of the stent comprises at least two of the ring structures being joined by a third plurality of connector segments, each of the third plurality of connector segments having an undulating portion;
   wherein said second axial portion of the stent is disposed between said first and third axial portions of the stent;
   wherein the undulating portion of each of the second plurality of connector segments is axially displaced from the undulating portion of a circumferentially adjacent connector segment when the stent is in said unexpanded configuration; and
   wherein the undulating portion of each of the first and third plurality of connector segments is axially aligned with the undulating portion of a circumferentially adjacent connector segment when the stent is in said unexpanded configuration.

12. The stent of claim 11, wherein each of the first, second and third plurality of connector segments is joined at one end to one of the peaks of the central regions of one of the ring structures and is joined at another end to one of the peaks of the central regions of an adjacent ring structure.

13. The stent of claim 12, wherein each of the first, second and third plurality of connector segments is generally straight along a longitudinal axis of the stent.

14. The stent of claim 13, wherein the undulating portion of each of the first, second and third plurality of connector segments is substantially identical to each other.

15. The stent of claim 14, wherein the second axial portion of the stent has about twice as many of the second plurality of connector segments joining adjacent ring structures as the first and third axial portions of the stent have of the first and third plurality of connector segments joining adjacent ring structures.

16. The stent of claim 15, wherein the undulating portion comprises a first u-shaped bend disposed between second and third u-shaped bends, the first u-shaped bend extending in a substantially opposite direction from the second and third u-shaped bends.

17. A stent having expanded and unexpanded configurations, said stent comprising:
   first and second ring structures individually comprising an endless undulating pattern and disposed axially adjacent each other;
   a first plurality of connector segments joining the first and second ring structures, each of the first plurality of connector segments having an undulating portion;
   a third ring structure comprising an endless undulating pattern and disposed axially adjacent the second ring structure; and
   a second plurality of connector segments joining the second and third ring structures, each of the second plurality of connector segments having an undulating portion;
   a fourth ring structure comprising an endless undulating pattern and disposed axially adjacent the third ring structure; and
   a third plurality of connector segments joining the third and fourth ring structures, each of the third plurality of connector segments having an undulating portion;
   a fifth ring structure comprising an endless undulating pattern and disposed axially adjacent the fourth ring structure; and
   a fourth plurality of connector segments joining the fourth and fifth ring structures, each of the fourth plurality of connector segments having an undulating portion;
   a sixth ring structure comprising an endless undulating pattern and disposed axially adjacent the fifth ring structure; and
   a fifth plurality of connector segments joining the fifth and sixth ring structures, each of the fifth plurality of connector segments having an undulating portion;
   a seventh ring structure comprising an endless undulating pattern and disposed axially adjacent the sixth ring structure;
   a sixth plurality of connector segments joining the sixth and seventh ring structures, each of the sixth plurality of connector segments having an undulating portion; and
   one or more pads extending outward from at least one of said first, second, third, fourth, fifth, sixth or seventh ring structures;
   wherein each of said one or more pads comprises an enlarged region spaced from at least one of said first, second, third, fourth, fifth, sixth or seventh ring structures by a narrow throat region;
   wherein the undulating portion of each connector segment of the third and fourth plurality of connector segments is axially displaced from the undulating portion of a circumferentially adjacent connector segment when the stent is in said unexpanded configuration; and wherein the undulating portion of each connector segment of the first, second, fifth and sixth plurality of connector segments is axially aligned with the undulating portion of a circumferentially adjacent connector segment when the stent is in said unexpanded configuration.

18. A stent having expanded and unexpanded configurations, said stent comprising:

a series of ring structures forming serpentine patterns comprising a plurality of unit structures, each unit structure comprising first and second lateral arms and a central region disposed between said first and second lateral arms, said central region having at least a peak disposed between first and second valleys, wherein the peak is shorter than the first and second lateral arms, each of said unit structures being inverted with respect to circumferentially adjacent unit structures, wherein the lateral arms of each unit structure are shared with the adjacent unit structures;

a plurality of connector segments comprising a undulating portion joining the ring structures together, each of the connector segments being joined at one end to one of the peaks of the central regions of one of the ring structures and being joined at another end to one of the peaks of the central regions of an adjacent ring structure;

wherein each of the plurality of connector segments is generally straight along a longitudinal axis of the stent; and wherein the undulating portion of each of the plurality of connector segments is substantially identical to each other.

19. The stent of claim 18, further comprising a first axial portion of the stent wherein the undulating portion of each connector segment is axially aligned with the undulating portion of a circumferentially adjacent connector segment when the stent is in said unexpanded configuration.

20. The stent of claim 19, further comprising a second axial portion of the stent wherein the undulating portion of each connector segment is axially displaced from the undulating portion of a circumferentially adjacent connector segment when the stent is in said unexpanded configuration.

* * * * *